United States Patent
Hiramura et al.

(10) Patent No.: US 10,130,584 B2
(45) Date of Patent: Nov. 20, 2018

(54) DISINTEGRATIVE PARTICLE COMPOSITION INCLUDING PULVERIZED LACTOSE OR GRANULATED LACTOSE

(71) Applicant: DAICEL CORPORATION, Osaka-shi, Osaka (JP)

(72) Inventors: Takahiro Hiramura, Minato-ku (JP); Kiyoshi Ikura, Himeji (JP); Tomohito Okabayashi, Himeji (JP); Yoshihisa Takigawa, Himeji (JP); Naohiro Hashikawa, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 15/524,023

(22) PCT Filed: Oct. 8, 2015

(86) PCT No.: PCT/JP2015/078566
§ 371 (c)(1),
(2) Date: May 3, 2017

(87) PCT Pub. No.: WO2016/084493
PCT Pub. Date: Jun. 2, 2016

(65) Prior Publication Data
US 2017/0340568 A1    Nov. 30, 2017

(30) Foreign Application Priority Data
Nov. 24, 2014 (JP) .................. 2014-237225

(51) Int. Cl.
| | |
|---|---|
| *A61K 9/20* | (2006.01) |
| *A61K 47/26* | (2006.01) |
| *A61K 47/36* | (2006.01) |
| *A61K 47/38* | (2006.01) |
| *A23L 33/10* | (2016.01) |
| *A23P 10/28* | (2016.01) |
| *A61K 9/16* | (2006.01) |

(52) U.S. Cl.
CPC ............ *A61K 9/2018* (2013.01); *A23L 33/10* (2016.08); *A23P 10/28* (2016.08); *A61K 9/1623* (2013.01); *A61K 9/1652* (2013.01); *A61K 9/20* (2013.01); *A61K 9/2013* (2013.01); *A61K 9/2054* (2013.01); *A61K 9/2059* (2013.01); *A61K 47/26* (2013.01); *A61K 47/36* (2013.01); *A61K 47/38* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2002/0061335 | A1* | 5/2002 | Kumar ................. | A61K 9/0014 424/488 |
| 2008/0085309 | A1* | 4/2008 | Tsushima ............. | A61K 9/0056 424/464 |

FOREIGN PATENT DOCUMENTS

| | | |
|---|---|---|
| JP | 56100801 | 8/1981 |
| JP | 1160507 | 3/1999 |
| JP | 2000273039 | 10/2000 |
| JP | 2004283135 | 10/2004 |
| JP | 2006063030 | 3/2006 |
| JP | 2006290972 | 10/2006 |
| JP | 3884056 | 2/2007 |
| JP | 2009203559 | 9/2009 |
| JP | 2011213695 | 10/2011 |
| WO | 2015163135 | 10/2015 |
| WO | 2013146917 | 12/2015 |
| WO | 2014046035 | 8/2016 |

OTHER PUBLICATIONS

International Search Report of application No. PCT/JP2015/078566 dated Dec. 15, 2015.

* cited by examiner

*Primary Examiner* — Robert A Wax
*Assistant Examiner* — Melissa S Mercier
(74) *Attorney, Agent, or Firm* — Ping Wang; Morris, Manning & Martin, LLP

(57) ABSTRACT

The purpose of the present invention is to provide a new disintegrative particulate composition having an optimal balance between the tablet hardness and disintegrability that are mutually opposing properties, and disintegrating tablets for pharmaceuticals and various kinds of foods comprising said composition.

The present invention relates to a disintegrative particulate composition comprising milled lactose and/or granulated lactose as an excipient, and to a disintegrating tablet for pharmaceuticals or foods, comprising the disintegrative particulate composition, especially the tablet having tablet hardness of from 20 to 200 N, and disintegration time in water of from 1 to 60 sec.

7 Claims, No Drawings

DISINTEGRATIVE PARTICLE COMPOSITION INCLUDING PULVERIZED LACTOSE OR GRANULATED LACTOSE

FIELD

The present invention relates to a disintegrative particulate composition comprising milled (pulverized) lactose or granulated lactose, and to various kinds of disintegrating tablets comprising said composition and having an excellent disintegrability and a high tablet moldability.

BACKGROUND

In the past, orally-disintegrating tablets have been developed in highly convenient forms which can safely be taken by patients who have difficulty in swallowing drugs, elderly people, children, etc. and which can easily be taken without water. It is important that orally-disintegrating tablets have sufficient breaking strength (tablet hardness) such that any cracks, powdering, etc. are not caused in the tablets during production or transportation of the tablets or during breaking the seals in the same manner as general tablets, and also, it is important that orally-disintegrating tablets have excellent disintegrability (disintegration time) such that the tablets immediately disintegrate in the oral cavity.

The tablet hardness and disintegrability are mutually opposing properties. In general, when a molding pressure is increased to increase the hardness, the disintegration time tends to be prolonged, and, when the molding pressure is reduced to shorten the disintegration time, the hardness tends to be smaller. Therefore, various technologies have been developed in order to cope with both the two properties or to achieve an optimal balance between the two properties. Furthermore, components of the particles, granulation methods, etc. have been studied in order to impart superior moldability to particles or particulate compositions constituting tablets.

The present inventors have already developed a method of producing a disintegrative particulate composition having an excellent disintegrability and tablet hardness, or having a higher tablet hardness without substantially extending disintegration time (Patent Literature (PTL) 1).

Furthermore, it has been developed a disintegrative particulate composition comprising the four components consisting of a first disintegrator component of an acid-type carboxymethylcellulose, a second disintegrator component other than the acid-type carboxymethylcellulose, an excipient of a sugar or sugar alcohol, and crystalline cellulose (PTL 2).

Furthermore, cellulose that is produced from a vegetable fiber and having a fiber diameter (a short diameter) or thickness of from about a few m to several hundreds nm has been generally known as "fine-fibrillated cellulose" or "micro-fibrillated cellulose." The production examples and its structure, properties and functions are described in PTL 5 and PTL 6 cited below.

In the fine- or micro-fibrillated cellulose, a surface area has been increased, hydrophilic property that is the original characteristics of cellulose has been significantly strengthened, and a three-dimensional network has been formed, without deteriorating basic properties such as physical and chemical stabilities of a starting material of cellulose. As a result, when it is formulated into goods in a paste or cream shape, it will show a water-retaining (syneresis-preventing) property and a form-retaining property due to the interaction with water and oil droplets, fine particles, etc. It is also utilized to modify goods in a jelly form, for example, to increase their strength.

Accordingly, the above cellulose has been widely used in various applications, for example, as a binder for powder and fibrous materials, a paper strong agent in papermaking, a thickening agent for improving food texture of foods, a humectant for water-retaining of foods, a filter aid for alcoholic beverage and the like.

As an application example of the micro-fibrillated cellulose, PTL 7 describes a gelly composition comprising a water-dispersible complex comprising the micro-fibrillated cellulose and a hydrophilic polymer that is soluble in warm water in a particular ratio; a gelling agent; and water in a particular ratio. It describes that the composition has properties to inhibit denaturation of proteins and precipitation of water-insoluble components during heating or warming treatment and to give a good food texture.

PTL 8 describes a gelling agent comprising a highly dispersible cellulose complex comprising the micro-fibrillated cellulose, a water-soluble polymer and hydrophilic substance in a particular ratio; and a particular kind of polysaccharide in a particular ratio. It describes that the agent is characterized as being superior in disintegration and dispersion in water when compared to a conventional highly dispersible cellulose complex, so that it can be used in industrial and practical dispersing conditions.

Thus, the micro-fibrillated cellulose is used as a one component in the gelly composition and gelling agent disclosed in PTL 7 and 8. Furthermore, the hydrophilic polymer is an essential component for the water-dispersible complex of PTL 7, and the water-soluble polymer is an essential component for the highly dispersible cellulose complex of PTL 8.

PTLs 3 and 4 disclose an orally-disintegrative particulate composition and an orally-disintegrating tablet, which comprise lactose. They are said to have an excellent disintegrability and practically sufficient hardness.

However, as described in an example of PTL 3, an orally-disintegrating tablet actually produced has hardness in a range of 40 and 60 N and oral disintegration time of dozens of seconds, which are not higher or faster than those of the other arts. Also, as described in an example of PTL 4, the hardness of an orally-disintegrating tablet produced using granulated lactose is 3.7 kgf (36N), which is not so high, either.

RELATED ARTS

Patent Literatures

PTL 1: International Publication Pamphlet WO2013/146917
PTL 2: International Publication Pamphlet WO2014/046035
PTL 3: JP-A-2000-273039
PTL 4: JP-A-2011-173848
PTL 5: JP-A-Sho 56-100801
PTL 6: JP-A-2009-203559
PTL 7: JP-A-2004-283135
PTL 8: JP-A-2006-290972

SUMMARY

Problems to be Solved by the Invention

It has not yet been obtained in the prior arts an orally-disintegrating tablet that was produced by using a disintegrative particulate composition comprising sieved lactose as an excipient, and having an optimal balance between the tablet hardness and disintegrability.

Accordingly, an object of the present invention is to solve such technical problems as mentioned above, and to provide a new disintegrative particulate composition having an excellent disintegrability and a high tablet moldability, and disintegrating tablets for pharmaceuticals and various kinds of foods, comprising said composition.

Means to Solve the Problem

The present inventors have earnestly studied and found that the above problems could be solved by using milled lactose or granulated lactose in place of or in addition to the sieved lactose that had been used in the conventional disintegrative particulate composition, leading to the completion of the present invention.

Thus, the present invention relates to the following aspects.

Aspect 1

A disintegrative particulate composition comprising milled lactose and/or granulated lactose as an excipient.

Aspect 2

The disintegrative particulate composition according to Aspect 1, further comprising micro-fibrillated cellulose.

Aspect 3

The disintegrative particulate composition according to Aspect 1 or 2, further comprising starch and processed starch as a disintegrator component.

Aspect 4

The disintegrative particulate composition according to Aspect 3, wherein the starch is corn starch, potato starch, waxy corn starch, α-starch and/or partially α-starch.

Aspect 5

The disintegrative particulate composition according to Aspect 4, wherein the starch is corn starch and/or partially α-starch.

Aspect 6

A disintegrating tablet for pharmaceuticals or foods, comprising the disintegrative particulate composition according to any one of Aspects 1-5.

Aspect 7

The disintegrating tablet according to Aspect 6, which has tablet hardness of from 20 to 200 N, and disintegration time in water of from 1 to 60 sec.

Aspect 8

The disintegrating tablet according to Aspect 7, which has tablet hardness of from 70 to 120 N, and disintegration time in water of from 15 to 30 sec.

Advantages of Invention

By using the disintegrative particulate composition comprising the milled lactose or granulate lactose as lactose, the tablet moldability of an orally-disintegrating tablet could be significantly improved while maintaining its excellent disintegrability.

The thus obtained orally-disintegrating tablet is useful as disintegrating tablets for pharmaceuticals and various kinds of foods such as such as supplemental foods, nutrition function foods and health foods, since it can safely be taken by patients who have difficulty in swallowing drugs, elderly people, children, etc. and which can be easily taken in a highly convenient form without water in any place.

Embodiments for Carrying Out the Invention

The present invention relates to the disintegrative particulate composition comprising milled lactose and/or granulated lactose as an excipient.

Lactose has been used as an additive in a solid pharmaceutical formulation as it has a low hygroscopicity, a high stability, flavoring with an appropriate sweetness, and is relatively cheap.

Lactose is generally produced using whey separated from milk as a source material through several crystallization, purification, washing with water, etc. The thus produced lactose will be further subjected to a physical step such as sieving, milling (pulverization), granulation, spray-drying, re-dissolving, and drying at a high temperature to give lactose with various grades (Pharma Teck Japan, 29 (13), 2013, 71 p-75 p).

The lactose produced through these physical steps are therefore generally defined in accordance with the production process, etc. as follows.

Sieved lactose: Lactose crystal is sieved to adjust its size distributions. As its particle size is relatively large, its powder flowability is high but its moldability is not good.

Milled lactose: Lactose crystal is milled or pulverized. As its particle size is relatively small, its moldability is high, but its powder flowability is not good. It is frequently utilized for the purpose of granulation Granulated lactose: It is one of lactose for direct tableting. It also includes a spray-drying product and a roller-drying product. It is provided with excellent flowability and moldability. The milled lactose is granulated by means of agitation granulation, fluidized-bed granulation, etc.

Since these various kinds of milled lactose and granulated lactose with various grades are commercially available from, for example, DFE Pharma or MEGGLE Co., LTD., they can be easily obtained.

The disintegrative particulate composition according to the present invention comprises milled lactose and/or granulated lactose as the excipient. Although it does not necessarily comprise sieved lactose as the excipient, it may comprise it. Furthermore, the sieved lactose may be mixed and used with the milled lactose and/or granulated lactose. The mixing ratio of the sieved lactose with the milled lactose and/or granulated lactose may be optionally determined by those skilled in the art depending on other components comprised in the disintegrative particulate composition, application of the composition, etc.

The disintegrative particulate composition according to the present invention may further comprise any sugars or sugar alcohols known in the art as an excipient.

The sugars or sugar alcohols include mannitol, erythritol, xylitol, trehalose, lactose, maltose, maltitol, glucose, sucrose, fructose, mannose, and sorbitol. Moreover, as preferable examples thereof, mannitol, erythritol, xylitol, trehalose, and lactose can be mentioned. As the sugars or sugar alcohols, two or more types of compounds properly selected from these compounds can also be used.

The disintegrative particulate composition according to the present invention may further comprise the micro-fibrillated cellulose. Any cellulose conventionally known as the "fine-fibrillated cellulose" or "micro-fibrillated cellulose" can be used as the "micro-fibrillated cellulose" in the present invention.

The micro-fibrillated cellulose is generally produced from the vegetable fiber and having the fiber diameter (the short diameter) or thickness of from about a few nm to 1 □m. The surface area of the the micro-fibrillated cellulose has been increased, its hydrophilic property that is the original characteristics of cellulose has been significantly strengthened, and its three-dimensional network has been formed, without deteriorating the basic properties such physical and chemical stabilities of the starting material of cellulose.

A dry material of the micro-fibrillated cellulose may be directly obtained in a dry state by any method known in the art, such as by directly pulverizing cellulose fiber in a dry state with a ball mill (PTL 5). Alternatively, the dry material of the micro-fibrillated cellulose may be obtained by subjecting the micro-fibrillated cellulose suspended in water, which was prepared by micro-fibrillation of water-dispersion of the cellulose fiber with a high-pressure homogenizer, to a solvent displacement stage, and removing the solvent in a drying stage, followed by pulverization in a pulverizing stage (PTL 6).

Preferable examples of the micro-fibrillated cellulose comprised in the disintegrative particulate composition according to the present invention include fiber assembly that has an average fiber length of 0.01~2 mm and an average fiber diameter of 0.001~1 μm, preferably of 0.01~0.1 μm (PTL 6). For example, such micro-fibrillated cellulose is commercially available with a trade name of "CELISH" series (a solid content of 10~35% in water) with various grades (an average fiber diameter of 0.01~0.1 μm) from Daicel FineChem Ltd.

As the other disintegrator components comprised in the disintegrative particulate composition of the present invention, any disintegrators known to a person skilled in the art, can be used. For example, it may comprise one or more components selected from crospovidone, croscarmellose sodium, low substituted hydroxypropylcellulose, carboxymethylcellulose calcium, starch such as corn starch, potato starch, waxy corn starch, α-starch or partially α-starch, and processed starch such as starch sodium glycolate and hydroxypropyl starch. Additionally, crospovidone is a common name for a cross-linked polymer of 1-vinyl-2-pyrrolidone, and croscarmellose sodium is a common name for a cross-linked product of carboxymethylcellulose sodium.

Among the above disintegrator components, starch and processed starch are preferable; corn starch, potato starch, waxy corn starch, α-starch and/or partially α-starch being more preferable; and corn starch and/or partially α-starch being most preferable.

Furthermore, in addition to the above-described components, various types of optional components known to a person skilled in the art may properly be added and mixed into the disintegrative particulate composition of the present invention, for the purpose of adjusting various characteristics such as the disintegrating force, binding force and ease in taking the tablet, without impairing the effects of the present invention by the above-described components. As examples of such components, disintegrators, auxiliary excipients, fluidizing agents, sweetening agents, corrigents, flavoring agents and coloring agents can be mentioned.

An amount of each component comprised in the disintegrative particulate composition of the present invention can properly be determined by a person skilled in the art, depending on, for example, the type of the component, the type and purpose of the disintegrating tablet, which is a target to be used for the disintegrative particulate composition. In general, relative to the total weight of the disintegrative particulate composition, the amount of lactose is within a range of 20% to 98% by weight, the amount of the micro-fibrillated cellulose (in terms of a dry weight) is within a range of 1% to 50% by weight, the amount of the other disintegrator components is within a range of 1% to 30% by weight.

The disintegrative particulate composition according to the present invention may be produced by any method or means known to a person skilled in the art.

For examples, the disintegrative particulate composition according to the present invention may be produced by mixing each of the components comprised in the composition all together.

Alternatively, it may be produced by various granulation processes. Any granulation method may be used, and a dry granulation process and a wet granulation process may be used to produce the composition.

The dry granulation process comprises the steps of mixing each powder of the components comprised in the disintegrative particulate composition optionally with an appropriate binder and the like, breaking the resulting mixture into small bulks with a high pressure, and appropriately crushing and granulating them. Examples of the dry granulation process include crushing granulation and roll-compressing method.

The wet granulation process is a method in which each component is dispersed in the presence of water, and the dispersion is dried to form complexes. As specific examples of the wet granulation process, spray methods such as spray drying, tumbling granulation, agitation granulation and fluidized-bed granulation; the freeze-drying method; kneading granulation, and the like can be mentioned, and the composition can be produced by any of these methods known to a person skilled in the art.

The disintegrative particulate composition according to the present invention may be produced by one wet granulation step using all of the components comprised therein together, or by adding and mixing each component in the plural wet granulation steps.

A person skilled in the art can properly determine which one or two types of the components comprised in the disintegrative particulate composition in the above plural wet granulation steps, depending on their types, amounts, etc.

Furthermore, a person skilled in the art can properly determine various conditions in the above plural wet granulation steps, such as the spraying speed, the supply air temperature, the exhaust temperature, and the air supply rate, depending on types or amounts of components, etc.

In each of the above granulation step, as a medium for the spray liquid, a solvent acceptable in pharmaceuticals or foods, such as water, ethanol, methanol or acetone, can be mentioned. Alternatively, as the spray liquid, for example, an aqueous solution in which less than 10% of the component(s) for the disintegrative particulate composition is dissolved can be mentioned, and, in particular, water or such an aqueous solution is preferable.

Each of the above components that may be optionally comprised in the disintegrative particulate composition according to the present invention may be optionally added in any of the above granulation steps. Alternatively, the above optional components may be added and mixed in an additionally-provided wet granulation step.

It is preferable that the disintegrative particulate composition of the present invention produced by the above wet granulation process has the following physical properties:

(1) an average particle size of 50 to 200 microns; and
(2) a water content of 0.5% to 6% by weight.

In addition, these physical properties are measured by using the following methods and conditions.

The average particle size: 2 g of the disintegrative particulate composition is subjected to a measurement with a Φ75 mm automatic shaking sieve device (Type "M-2", Tsutsui Scientific Instruments Co., Ltd.).

The water content: 5 g of the disintegrative particulate composition is subjected to a measurement using a halogen water content measuring device (Type "HB43", METTLER TOLEDO K.K.).

The present invention also relates to a disintegrating tablet comprising the above disintegrative particulate composition, especially to an orally disintegrating tablet for pharmaceuticals or foods such as supplemental foods, nutrition function foods and health foods. The content of the disintegrative particulate composition in the disintegrating tablet can properly be determined by a person skilled in the art, depending on, for example, the application and purpose of the disintegrating tablet, without impairing the effects of the present invention. There is no particular limitation on the shape or form of the tablet.

The disintegrating tablet has the excellent tablet hardness and disintegrability since it comprises the disintegrative particulate composition of the present invention. As shown by the examples, it is characterized by having a hardness of 20 to 200 N and a disintegration time in water of 1 to 60 seconds, preferably having a hardness of 30 to 150 N and a disintegration time in water of 1 to 45 seconds, more preferably having a hardness of 70 to 120 N and a disintegration time in water of 15 to 30 seconds.

The disintegrating tablet according to the present invention may optionally comprise any other components than the disintegrative particulate composition.

The disintegrating tablet for foods may optionally comprise, for example, various nutritional components such as proteins, carbohydrates, lipids and minerals; various vitamins and their derivatives; and designated or existing additives according to Food Sanitation Law, Art. 10; and other components acceptable as a food component (a food additive) listed in a list of general additives for food and drink, such as acidulants, sweeteners, excipients, surfactants, lubricants, corrigents, flavoring agents, colorants, and stabilizing agents, The orally disintegrating tablet for pharmaceuticals may optionally comprise, for example, in addition to a medicinal ingredient and said disintegrative particulate composition, other components acceptable as additives from a pharmaceutical or food-sanitary point of view, such as excipients, surfactants, lubricants, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliary agents. Also, the blending ratios of the disintegrative particulate composition, the medicinal ingredient and each optional ingredient (component) are not particularly limited as long as the expected effects of the present invention are brought about, and the blending ratios can properly be determined by those skilled in the art. The orally disintegrating tablet can be formulated by any methods known to those skilled in the art, for example, by tableting. There is no limitation on an application or kind of the medicinal ingredients comprised in the orally disintegrating tablet according to the present invention, which may include, for example, agents affecting each organ such as the central nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such as an agent activating cellular function, an agent affecting tumors, an radioactive medicine, an anti-allergic agent; medicines based on a medical prescription relating to herbal medicines and Chinese medicines; antibiotics; agents for chemotherapy, biological drug; agents for pathogenic organisms such as parasites; agents for formulation use, diagnosis, public health and in-vitro diagnosis.

In addition, contents of all related art documents cited in the present specification are incorporated herein by reference.

Hereinafter, the present invention will more specifically be described with reference to Examples. However, the present invention is not considered to be limited to the Examples.

Evaluation on Hardness and Disintegrability Tests

Values of the hardness and disintegration time in water of the tablets obtained in the Examples and Comparative Example were measured based on the following conditions/methods.

Hardness: a hardness (N) was measured with a digital Kiya hardness tester (Fujiwara Scientific Company Co., Ltd.).

Disintegration time in water: a disintegration time in water was measured with a disintegration tester (NT-400, TOYAMA SANGYO CO., LTD.) in accordance with the method described in the Japanese Pharmacopoeia provided that an auxiliary disk was not used.

The measurements for the hardness and disintegration time were each repeated six times, and average values thereof were regarded as measurement results.

EXAMPLE 1

Production of Disintegrative Particulate Composition 1

270 g of milled lactose (GranuLac, MEGGLE Co., LTD), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-200L", Daicel FineChem Ltd.) in water was sprayed onto the resulting mixture at a rate of 12 g/minute, so that the mixture was granulated to thereby obtain disintegrative particulate composition 1. The resulting disintegrative particulate composition 1 had the following values for physical properties: (1) an average particle size of 103 microns and (2) a water content of 3.1% by weight.

Production of Orally Disintegrating Tablet 1

99.5 parts by weight of the resulting disintegrative particulate composition 1 was mixed with 0.5 parts by weight of magnesium stearate (Taihei Chemical Industrial Co. Ltd.). The mixture was then subjected to tableting at a tablet compression force of from 6 to 8 Kn with a simple tableting machine (HANDTAB-100, ICHIHASHI-SEIKI Co., Ltd.) to thereby obtain an angled-corner flat tablet having a diameter of 8.0 mm and a weight of 250 mg.

EXAMPLE 2

Production of Disintegrative Particulate Composition 2

270 g of granulated lactose (FlowLac, MEGGLE Co., LTD), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-200L", Daicel FineChem Ltd.) in water was sprayed onto the resulting mixture at a rate of 12 g/minute, so that the mixture was granulated to thereby obtain disintegrative particulate composition 2. The resulting disintegrative particulate composition 2 had the following values for physical properties: (1) an average particle size of 169 microns and (2) a water content of 2.3% by weight.

Production of Orally Disintegrating Tablet 2

The resulting disintegrative particulate composition 2 was subjected to tableting in the same manner as Example 1 to thereby obtain an angled-corner flat tablet having a diameter of 8.0 mm and a weight of 250 mg.

EXAMPLE 3

Production of Disintegrative Particulate Composition 3

54 g of sieved lactose (SpheroLac, MEGGLE Co., LTD), 216 g of milled lactose (GranuLac, MEGGLE Co., LTD), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-200L", Daicel FineChem Ltd.) in water was sprayed onto the resulting mixture at a rate of 12 g/minute, so that the mixture was granulated to thereby obtain disintegrative particulate composition 3. The resulting disintegrative particulate composition 3 had the following values for physical properties: (1) an average particle size of 136 microns and (2) a water content of 3.0% by weight.

Production of Orally Disintegrating Tablet 3

The resulting disintegrative particulate composition 3 was subjected to tableting in the same manner as Example 1 to thereby obtain an angled-corner flat tablet having a diameter of 8.0 mm and a weight of 250 mg.

EXAMPLE 4

Production of Disintegrative Particulate Composition 4

135 g of sieved lactose (SpheroLac, MEGGLE Co., LTD), 135 g of milled lactose (GranuLac, MEGGLE Co., LTD), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-200L", Daicel FineChem Ltd.) in water was sprayed onto the resulting mixture at a rate of 12 g/minute, so that the mixture was granulated to thereby obtain disintegrative particulate composition 4. The resulting disintegrative particulate composition 4 had the following values for physical properties: (1) an average particle size of 142 microns and (2) a water content of 3.2% by weight.

Production of Orally Disintegrating Tablet 4

The resulting disintegrative particulate composition 4 was subjected to tableting in the same manner as Example 1 except tableting at a tablet compression force of from 8 to 10 kN to thereby obtain an angled-corner flat tablet having a diameter of 8.0 mm and a weight of 250 mg.

COMPARATIVE EXAMPLE 1

270 g of sieved lactose (SpheroLac, MEGGLE Co., LTD), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-200L", Daicel FineChem Ltd.) in water was sprayed onto the resulting mixture at a rate of 12 g/minute, so that the mixture was granulated to thereby obtain disintegrative particulate composition. The resulting disintegrative particulate composition had the following values for physical properties: (1) an average particle size of 157 microns and (2) a water content of 2.7% by weight.

Production of Orally Disintegrating Tablet 99.5 parts by weight of the resulting disintegrative particulate composition 1 was mixed with 0.5 parts by weight of magnesium stearate (Taihei Chemical Industrial Co. Ltd.). The mixture was then subjected to tableting at a tablet compression force of from 8 to 10 kN with a simple tableting machine (HANDTAB-100, ICHIHASHI-SEIKI Co., Ltd.) to thereby obtain an angled-corner flat tablet having a diameter of 8.0 mm and a weight of 250 mg.

Evaluation of the Test of Hardness and Disintegration Time

The above Examples and Comparative Example were measured with respect to their hardness and disintegration time in water based on the following conditions/methods. The test results of hardness and disintegration time are shown in Table 1.

TABLE 1

| Orally Disintegrating Tablet | Example 1 | | Example 2 | |
|---|---|---|---|---|
| Tablet Compression Force (kN) | 6 | 8 | 6 | 8 |
| Tablet Hardness (N) | 74 | 100 | 61 | 84 |
| Disintegration Time in Water (s) | 21 | 24 | 15 | 18 |

| Orally Disintegrating Tablet | Example 3 | | Example 4 | |
|---|---|---|---|---|
| Tablet Compression Force (kN) | 8 | 10 | 8 | 10 |
| Tablet Hardness (N) | 78 | 94 | 73 | 92 |
| Disintegration Time in Water(s) | 22 | 29 | 25 | 23 |

| Orally Disintegrating Tablet | Comparative Example 1 | |
|---|---|---|
| Tablet Compression Force (kN) | 8 | 10 |
| Tablet Hardness (N) | 49 | 60 |
| Disintegration Time in Water (s) | 12 | 12 |

The results shown in Table 1 demonstrate that the orally-disintegrating tablets, which are produced by using the disintegrative particulate composition comprising the milled lactose and/or granulated lactose in place of or in addition to the conventionally-used sieved lactose, have an optimal balance between the tablet hardness and disintegrability, that is, a high tablet moldability and an excellent disintegrability, when compared with the orally-disintegrating tablets produced by using the disintegrative particulate composition comprising the sieved lactose only as lactose.

INDUSTRIAL APPLICABILITY

The present invention significantly contributes to research and development of disintegrating tablets having excellent tablet hardness and disintegrability.

The invention claimed is:

1. A disintegrative particulate composition comprising
milled lactose and/or granulated lactose as an excipient, and
micro-fibrillated cellulose,
where in the micro-fibrillated cellulose is produced only by physical processing of natural cellulose.

2. The disintegrative particulate composition according to claim 1, further comprising starch and/or processed starch as disintegrator component(s).

3. The disintegrative particulate composition according to claim 2, wherein the starch is corn starch, potato starch, waxy corn starch, a-starch and/or partially α-starch.

4. The disintegrative particulate composition according to claim 3, wherein the starch is corn starch and/or partially α-starch.

5. A disintegrating tablet for pharmaceuticals or foods, comprising the disintegrative particulate composition according to claim 1.

6. The disintegrating tablet according to claim 5, which has tablet hardness of from 20 to 200 N, and disintegration time in water of from 1 to 60 sec.

7. The disintegrating tablet according to claim 6, which has tablet hardness of from 70 to 120 N, and disintegration time in water of from 15 to 30 sec.

* * * * *